United States Patent
Okamoto et al.

(10) Patent No.: US 7,453,005 B2
(45) Date of Patent: Nov. 18, 2008

(54) TRANSITION METAL COMPOUND AND CATALYST FOR OLEFIN POLYMERIZATION

(75) Inventors: Takuji Okamoto, Ichihara (JP); Takashi Kashiwamura, Ichihara (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 43 days.

(21) Appl. No.: 10/584,057

(22) PCT Filed: Jan. 24, 2005

(86) PCT No.: PCT/JP2005/000858

§ 371 (c)(1),
(2), (4) Date: Jun. 22, 2006

(87) PCT Pub. No.: WO2005/073242

PCT Pub. Date: Aug. 11, 2005

(65) Prior Publication Data

US 2007/0161502 A1 Jul. 12, 2007

(30) Foreign Application Priority Data

Jan. 28, 2004 (JP) .............................. 2004-020492

(51) Int. Cl.
C07F 17/00 (2006.01)
C07F 5/02 (2006.01)
C07F 9/28 (2006.01)
(52) U.S. Cl. ................. 556/7; 556/13; 556/53
(58) Field of Classification Search ............ 556/7, 556/21, 53; 526/134, 160, 161; 502/152, 502/162, 202
See application file for complete search history.

(56) References Cited

U.S. PATENT DOCUMENTS

| 6,583,239 B2 * | 6/2003 | Minami et al. ............... 526/127 |
| 6,730,626 B2 | 5/2004 | Kashiwamura et al. |
| 7,214,755 B2 * | 5/2007 | Minami et al. ........... 526/348.3 |

FOREIGN PATENT DOCUMENTS

| EP | 0 468 651 | 1/1992 |
| EP | 0 661 300 | 7/1995 |
| JP | 58-19309 | 2/1983 |
| JP | 60-217209 | 10/1985 |
| JP | 1-502636 | 9/1989 |
| JP | 03-139504 | 6/1991 |
| JP | 03-207704 | 9/1991 |
| WO | 92/01723 | 2/1992 |
| WO | 93/20113 | 10/1993 |

OTHER PUBLICATIONS

U.S. Appl. No. 10/584,057, filed Jun. 22, 2006, Okamoto et al.

Brandow, Christopher G. et al., "Ancillary Ligand and Olefin Substituent Effects on Olefin Dissociation for Cationic Zirconocene Complexes Bearing a Coordinated Pendant Olefin", Organometallics, vol. 20, No. 20, pp. 4253-4261, 2001.

Breslow, David S. et al., "Bis-(cyclopentadienyl)-titanium Dichloride-Alkylaluminum Complexes as Soluble Catalysts for the Polymerization of Ethylene[1, 2]", Journal of the American Chemical Society, vol. 81, pp. 81-87, Jan. 5, 1959.

Roberts, Royston M. et al., "Malononitrile", Journal of the American Chemical Society, vol. 82, pp. 1952-1957, Apr. 20, 1960.

Eisch, John J. et al., "Direct Observation of the Initial Insertion of an Unsaturated Hydrocarbon into the Titanium-Carbon Bond of the Soluble Ziegler Polymerization ctalayst, Cp2TiCl2-MeAlcl2[1]", Journal of American Chemical Society, vol. 107, No. 24, pp. 7219-7221, Nov. 27, 1985.

Jordan. Richard F. et al., "Ethylene Polymerization by a Cationic Dicyclopentadienylzirconium (IV) Alkyl Complex", Journal of American chemical Society, vol. 108, No. 23, pp. 7410-7411, Nov. 12, 1986.

(Continued)

Primary Examiner—Caixia Lu
(74) Attorney, Agent, or Firm—Oblon, Spivak, McClelland, Maier & Neustadt, P.C.

(57) ABSTRACT

A transition metal compound useful as a component of a catalyst for olefin polymerization and a highly active polymerization catalyst capable of producing a high molecular weight olefin polymer. The catalyst for olefin polymerization contains a transition metal compound represented by formula (1)

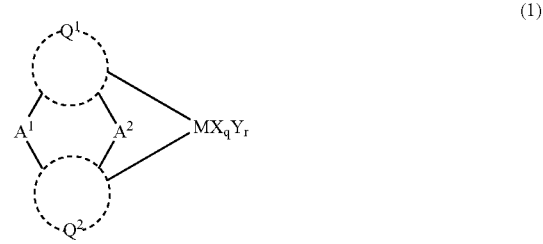

(1)

wherein M is a metal element of the groups 3 to 10 of the Periodic Table or a lanthanoid; X represents a ligand having a sigma bond for binding to M, and when X is plural, the Xs may be the same or different; Y represents a Lewis base, and when Y is plural, the Ys may be the same or different; $A^1$ and $A^2$ represent crosslinking groups and at least one thereof has a boron or phosphorous atom as a crosslinking atom; q is an integer of 1 to 5 and equals [(the valance of M)−2]; r is an integer of 0 to 3; and $Q^1$ and $Q^2$ have a specific structure, and $Q^1$ and $Q^2$ may be different or the same.

1 Claim, No Drawings

OTHER PUBLICATIONS

Mengele, Winfried et al. "ansa-Metallocene Derivatives. 27. Chiral Zirconocene Complexes with Two Dimethylsilylene Bridges[1]", Organometallics, vol. 12, No. 5, pp. 1931-1935, May 1993.

Dorer, Birgit et al., "Syntheses and Structures of Titanocene, Zirconocene, and Vanadocene Dichloride Complexes with Two Ethanediyl Bridges[1]", Organometallics, vol. 13, No. 10, pp. 3868-3872, Oct. 1994.

Hays, Melanie L. et al., "Steric Influence on the Structure, Magnetic Properties, and Reactivity of Hexa-and Octaisopropylmanganocene", Organometallics, vol. 17, No. 25, pp. 5521-5527, Dec. 7, 1998.

Herzog, Timothy A. et al., "A New Class of Zirconocene Catalysts for the Syndiospecific Polymerization of Propylene and Its Modification for Varying Polypropylene from Isotactic to Syndiotactic", Journal of American Chemical Society, vol. 118, No. 27, pp. 11988-11989, Nov. 27, 1996.

* cited by examiner

TRANSITION METAL COMPOUND AND CATALYST FOR OLEFIN POLYMERIZATION

TECHNICAL FIELD

The invention relates to a transition metal compound and a catalyst for olefin polymerization.

BACKGROUND ART

Conventionally, a catalyst comprising a transition metal compound and aluminoxane has been known as a highly active soluble olefin polymerization catalyst (for example, refer to Japanese Patent Applications Laid-open No. 58-19309 and No. 60-217209).

In addition, cations have been reported to be effective as an active species for a soluble olefin polymerization catalyst (for example, refer to J. Am. Chem. Soc., vol. 81, page 81 (1959); J. Am. Chem. Soc., vol. 82, page 1953 (1960), or J. Am. Chem. Soc., vol. 107, page 7219 (1986)).

As examples of the catalyst applying the separated active species to olefin polymerization, J. Am. Chem. Soc., vol. 108, page 7410 (1986), Published Japanese Translation of PCT Application No. 1-502636, Japanese Patent Application Laid-open No. 3-139504, European Patent Application Publication No. 468651, and the like can be given. In addition, as examples of a catalyst using this active species combined with an organoaluminum compound, Japanese Patent Application Laid-open No. 3-207704, International Patent Publication Pamphlet No. 92/1723, and the like can be given.

On the other hand, there are only a few reports on the use of a multiplex crosslinking (double crosslinking) metallocene complex. International Patent Publication Pamphlet No. 93/20113, Organometallics, vol. 12, page 1931 (1993), Organometallics, vol. 13, page 3868, Organometallics, vol. 17, page 5525, and J. Am. Chem. Soc., vol. 118, page 11988 have a report on this subject.

Regarding the behavior as the polymerization catalyst, Organometallics, vol. 12, page 1931 (1993) describes an example of propylene polymerization. According to the report, it is necessary to divide meso isomers of a metallocene complex from racemic isomers in order to obtain isotactic polypropylene. In addition, the resulting polypropylene has a low molecular weight.

The molecular weight of polypropylene was also small in the study on the polymerization of propylene reported by Bercaw in J. Am. Chem. Soc., vol. 118, page 11988.

DISCLOSURE OF THE INVENTION

The invention has been made in view of the above problems and has an object of providing (1) a novel transition metal compound (a double crosslinking metallocene complex) useful as a component of a catalyst for olefin polymerization, (2) a highly active polymerization catalyst capable of producing a high molecular weight olefin polymer, (3) high molecular weight homopolymer and copolymer of olefins obtained by using this polymerization catalyst, and (4) a method for efficiently producing the above-mentioned olefin polymers.

As a result of extensive studies to achieve the above object, the present inventors have found that a novel transition metal compound having a specific structure is useful as a component of a catalyst for olefin polymerization and that a polymerization catalyst comprising this transition metal compound and an activating co-catalyst is highly active and can produce an olefin polymer with a high molecular weight and a narrow molecular weight distribution. These findings has led to completion of the invention.

According to the invention, a transition metal compound represented by formula (1) is provided,

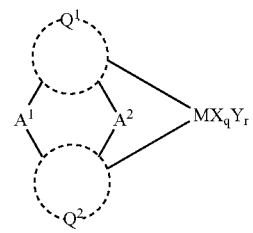

(1)

wherein M is a metal element of the groups 3 to 10 of the periodic table or a lanthanoid; X represents a ligand having a sigma bond for binding to M, and when X is plural, the Xs may be the same or different; Y represents a Lewis base, and when Y is plural, the Ys may be the same or different; $A^1$ and $A^2$ represent crosslinking groups and at least one thereof has a boron or phosphorous atom as a crosslinking atom; q is an integer of 1 to 5 and equals [(the atomic valence of M)−2]; r is an integer of 0 to 3; and $Q^1$ and $Q^2$ have a structure represented by formula (2) or (3), and $Q^1$ and $Q^2$ may be different or the same,

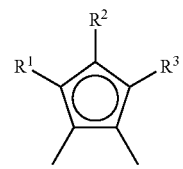

(2)

wherein $R^1$ to $R^3$ are a hydrogen atom, a halogen atom, a hydrocarbon group with 1 to 20 carbon atoms, a halogen-containing hydrocarbon group with 1 to 4 carbon atoms, a silicon-containing group, or a hetero-atom-containing group,

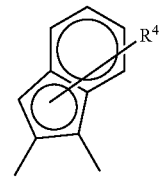

(3)

wherein $R^4$ is a hydrogen atom or a hydrocarbon group with 1 to 20 carbon atoms.

In addition, a catalyst for olefin polymerization containing this transition metal compound (A) is provided.

Moreover, a method for producing an olefin polymer comprising homo-polymerizing an olefin, or co-polymerizing an olefin with another olefin and/or another monomer in the presence of the catalyst for olefin polymerization is provided.

Furthermore, an olefin polymer obtainable by this production method is provided.

The transition metal compound of the invention is useful as a catalyst component for olefin polymerization. A high molecular weight polyolefin possessing regularity can be obtained by using the catalyst for olefin polymerization containing the transition metal compound of the invention.

BEST MODE FOR CARRYING OUT THE INVENTION (1) Transition Metal Compound

The transition metal compound of the invention has a chemical structure represented by the formula (1).

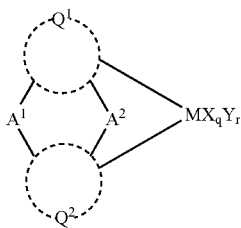

(1)

This transition metal compound has a double crosslinked, substituted or unsubstituted cyclopentadienyl group and/or an indenyl group, with at least one of $A^1$ and $A^2$ being crosslinked using a boron or phosphorous atom as a crosslinking atom.

In the formula (1), $A^1$ and $A^2$ have a structure represented by formula (4) or (5), for example,

(4)

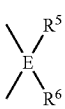

(5)

wherein E represents a crosslinking atom which is, for example, an element of the groups 13 to 15 of the periodic table. At least one of $A^1$ and $A^2$ has a boron or phosphorous atom as a crosslinking atom.

$R^5$ represents a hydrocarbon group having 1 to 20 carbon atoms. As specific examples, alkyl groups such as a methyl group, ethyl group, propyl group, butyl group, hexyl group, cyclohexyl group, and octyl group; alkenyl groups such as a vinyl group, propenyl group, and cyclohexenyl group; arylalkyl groups such as a benzyl group, phenylethyl group, and phenylpropyl group; and aryl groups such as a phenyl group, tolyl group, dimethylphenyl group, trimethylphenyl group, ethylphenyl group, propylphenyl group, biphenyl group, naphthyl group, methylnaphthyl group, anthracenyl group, and phenanthryl group can be given.

When E is a boron atom, $R^5$ represents an electrically neutral basic group containing nitrogen, oxygen, phosphorous, or sulfur, or a group having a negative charge containing an alkyl anion, allyl anion, or $N^-$.

As specific examples of the electrically neutral basic group containing nitrogen, oxygen, phosphorous, or sulfur, trimethylamine, triethylamine, diethyl ether, tetrahydrofuran, trimethyl phosphine, and dimethyl sulfide can be given.

As specific examples of the group having a negative charge containing an alkyl anion, allyl anion, or $N^-$, alkyl groups such as a methyl group, ethyl group, propyl group, butyl group, hexyl group, cyclohexyl group, and octyl group; alkenyl groups such as a vinyl group, propenyl group, and cyclohexenyl group; arylalkyl groups such as a benzyl group, phenylethyl group, and phenylpropyl group; aryl groups such as a phenyl group, tolyl group, dimethylphenyl group, trimethylphenyl group, ethylphenyl group, propylphenyl group, biphenyl group, naphthyl group, methylnaphthyl group, anthracenyl group, and phenanthryl group; nitrogen-containing groups such as a dimethylamino group, diisopropylamino group, and diphenyl amino group can be given.

When E is a phosphorous atom, given as examples of $R^6$ are groups that form a multiple bond with E such as =O, =N—R, =S, and =$CR^7R^8$, wherein $R^7$ and $R^8$ represent alkyl groups such as a methyl group, ethyl group, propyl group, butyl group, hexyl group, cyclohexyl group, and octyl group; alkenyl groups such as a vinyl group, propenyl group, and cyclohexenyl group; arylalkyl groups such as a benzyl group, phenylethyl group, and phenylpropyl group; and aryl groups such as a phenyl group, tolyl group, dimethylphenyl group, trimethylphenyl group, ethylphenyl group, propylphenyl group, biphenyl group, naphthyl group, methylnaphthyl group, anthracenyl group, and phenanthryl group.

When E is a phosphorous atom, an oxo group, methylimino group, phenylimino group, trimethylsilylimino group, thio group, =$C(CH_3)_2$, and =$CPh_2$ can be given as specific examples of $R^6$.

As specific examples of the crosslinking group, B—$CH_3$, B-Ph, B—$N(i-Pr)_2$, and B—$CH_3(NEt_3)$ can be given when E is a boron atom.

P—$CH_3$, P-Ph, P(O)Ph, P($NSi(CH_3)_3$)Ph, and the like can be given when E is a phosphorous atom.

In this specification, Ph stands for a phenyl group, Me stands for a methyl group, Et stands for an ethyl group, and Pr stands for a propyl group. These abbreviations are used from time to time in the following description.

As the crosslinking group not containing phosphorous and boron, for example, substituted silyl groups such as dimethylsilylene, diethylsilylene, diisopropylsilylene, methylisopropylsilylene, diphenylsilylene, di(p-tolyl)silylene, methylphenylsilylene, and ethylphenylsilylene; substituted disilyl groups such as a tetramethyldisilyl group and dimethyldiphenyldisilyl group; and hydrocarbon groups such as isopropylidene, diphenylmethylene, methylphenylmethylene, ethylidene, methylene, ethylene, tetramethylethylene, cyclohexylidene, 1,2-cyclohexylene, 1,2-phenylene, vinylene, vinylidene, and ethenylidene ($CH_2$=C=) can be used.

A crosslinking group shown by the formula (6) is preferable.

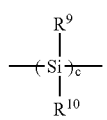

(6)

wherein $R^9$ and $R^{10}$ are a hydrogen atom or a hydrocarbon group having 1 to 20 carbon atoms, and c is an integer of 1 to 4.

As specific examples of the hydrocarbon group having 1 to 20 carbon atoms, alkyl groups such as a methyl group, ethyl group, propyl group, butyl group, hexyl group, cyclohexyl group, and octyl group; alkenyl groups such as a vinyl group, propenyl group, and cyclohexenyl group; arylalkyl groups such as a benzyl group, phenylethyl group, and phenylpropyl group; and aryl groups such as a phenyl group, tolyl group, dimethylphenyl group, trimethylphenyl group, ethylphenyl group, propylphenyl group, biphenyl group, naphthyl group, methylnaphthyl group, anthracenyl group, and phenanthryl group can be given.

In the formula (1), M is a metal element of the groups 3 to 10 of the periodic table or a lanthanoid. As specific examples, titanium, zirconium, hafnium, vanadium, chromium, manganese, nickel, cobalt, palladium, and lanthanoid metals can be given. Of these metals, titanium, zirconium, and hafnium are suitable.

X represents a sigma-bonding ligand. Specific examples include a halogen atom, hydrocarbon group having 1 to 20 carbon atoms, alkoxy group having 1 to 20 carbon-atoms, aryloxy group having 6 to 20 carbon atoms, amide group having 1 to 20 carbon atoms, silicon-containing group having 1 to 20 carbon atoms, phosphido group having 1 to 20 carbon atoms, sulfide group having 1 to 20 carbon atoms, and acyl group having 1 to 20 carbon atoms. q is an integer of 1 to 5 and equals [(the atomic valence of M)–2] and when q is two or more, a plurality of Xs may be the same or different.

As the halogen atom, a chlorine atom, fluorine atom, bromine atom, and iodine atom can be given.

As specific examples of the hydrocarbon group having 1 to 20 carbon atoms, alkyl groups such as a methyl group, ethyl group, propyl group, butyl group, hexyl group, cyclohexyl group, and octyl group; alkenyl groups such as a vinyl group, propenyl group, and cyclohexenyl group; arylalkyl groups such as a benzyl group, phenylethyl group, and phenylpropyl group; and aryl groups such as a phenyl group, tolyl group, dimethylphenyl group, trimethylphenyl group, ethylphenyl group, propylphenyl group, biphenyl group, naphthyl group, methylnaphthyl group, anthracenyl group, and phenanthryl group can be given.

As examples of the alkoxy group having 1 to 20 carbon atoms, alkoxy groups such as a methoxy group, ethoxy group, propoxy group, and butoxy group, phenylmethoxy group, and phenylethoxy group can be given.

As examples of the aryloxy group having 6 to 20 carbon atoms, a phenoxy group, methylphenoxy group, and dimethylphenoxy group can be given.

As examples of the amide group having 1 to 20 carbon atoms, alkylamide groups such as a dimethylamide group, diethylamide group, dipropylamide group, dibutylamide group, dicyclohexylamide group, and methylethylamide group; alkenylamide groups such as a divinylamide group, dipropenylamide group, and dicyclohexenylamide group; arylalkylamide groups such as a dibenzylamide group, phenylethylamide group, and phenylpropylamide group; and arylamide groups such as a diphenylamide group and dinaphtylamide group can be given.

As examples of the silicon-containing group having 1 to 20 carbon atoms, mono-hydrocarbon-substituted silyl groups such as a methylsilyl group and phenylsilyl group; di-hydrocarbon-substituted silyl groups such as a dimethylsilyl group and diphenylsilyl group; tri-hydrocarbon-substituted silyl groups such as a trimethylsilyl group, triethylsilyl group, tripropylsilyl group, dimethyl (t-butyl) silyl group, tricyclohexylsilyl group, triphenylsilyl group, dimethylphenylsilyl group, methyldiphenylsilyl group, tritolylsilyl group, and trinaphthylsilyl group; hydrocarbon substituted silyl ether groups such as a trimethyl silyl ether group; silicon-substituted alkyl groups such as a trimethylsilylmethyl group; silicon-substituted aryl groups such as a trimethylsilylphenyl group; dimethylhydrosilyl group, methyldihydrosilyl group, and the like can be given.

As specific examples of the phosphido group having 1 to 20 carbon atoms, a dimethylphosphido group, methylphenylphosphido group, diphenylphosphido group, dicyclohexylphosphido group, dibenzylphosphido group, and the like can be given.

As examples of the sulfide group having 1 to 20 carbon atoms, alkylsulfide groups such as a methylsulfide group, ethylsulfide group, propylsulfide group, butylsulfide group, hexylsulfide group, cyclohexylsulfide group, and octylsulfide group; alkenylsulfide groups such as a vinylsulfide group, propenylsulfide group, and cyclohexenylsulfide group; arylalkylsulfide groups such as a benzylsulfide group, phenylethylsulfide group, and phenylpropylsulfide group; and arylsulfide groups such as a phenylsulfide group, tolylsulfide group, dimethylphenylsulfide group, trimethylphenylsulfide group, ethylphenylsulfide group, propylphenylsulfide group, biphenylsulfide group, naphthylsulfide group, methylnaphthylsulfide group, anthracenylsulfide group, and phenanthrylsulfide group can be given.

As examples of the acyl group having 1 to 20 carbon atoms, alkylacyl groups such as a formyl group, acetyl group, propionyl group, butyryl group, valeryl group, palmitoyl group, stearoyl group, and oleoyl group; arylacyl groups such as a benzoyl group, toluoyl group, salicyloyl group, cinnamoyl group, naphthoyl group, and phthaloyl group; and oxalyl groups, malonyl groups, and succinyl groups which are derived from dicarboxylic acids of, respectively, oxalic acid, malonic acid, and succinic acid can be given.

Y represents a Lewis base. As specific examples, amines, ethers, phosphines, and thioethers can be given. r is an integer of 0 to 3.

As the amines, amines having 1 to 20 carbon atoms can be given. Specific examples include alkyl amines such as methylamine, ethylamine, propylamine, butylamine, cyclohexylamine, methylethylamine, dimethylamine, diethylamine, dipropylamine, dibutylamine, dicyclohexylamine, methylethylamine, trimethylamine, triethylamine, and tri-n-butylamine; alkenylamines such as vinylamine, propenylamine, cyclohexenylamine, divinylamine, dipropenylamine, and dicyclohexenylamine; arylalkylamines such as phenylmethylamine, phenylethylamine, and phenylpropylamine; arylamines such as diphenylamine and dinaphthyl amine; ammonia, aniline, N-methylaniline, diphenylamine, N,N-dimethylaniline, methyl diphenylamine, pyridine, and p-bromo-N,N-dimethylaniline.

As specific examples of the ether, simple aliphatic ether compounds such as methyl ether, ethyl ether, propyl ether, isopropyl ether, butyl ether, isobutyl ether, n-amyl ether, and isoamyl ether; mixed aliphatic ether compounds such as methyl ethyl ether, methyl propyl ether, methyl isopropyl ether, methyl n-amyl ether, methyl isoamyl ether, ethyl propyl ether, ethyl isopropyl ether, ethyl butyl ether, ethyl isobutyl ether, ethyl n-amyl ether, and ethyl isoamyl ether; aliphatic unsaturated ether compounds such as vinyl ether, allyl ether, methyl vinyl ether, methyl allyl ether, ethyl vinyl ether, and ethyl allyl ether; aromatic ether compounds such as anisole, phenetole, phenyl ether, benzyl ether, phenyl benzyl ether, α-naphthyl ether, and β-naphthyl ether; and cyclic ether compounds such as ethylene oxide, propylene oxide, trimethylene oxide, tetrahydrofuran, tetrahydropyrane, and dioxane can be given.

As the phosphine, phosphines having 1 to 20 carbon atoms can be given. Specific examples are alkyl phosphines, which include mono-hydrocarbon-substituted phosphines such as methylphosphine, ethylphosphine, propylphosphine, butylphosphine, hexylphosphine, cyclohexylphosphine, and octylphosphine; di-hydrocarbon-substituted phosphines such as dimethylphosphine, diethylphosphine, dipropylphosphine, dibutylphosphine, dihexylphosphine, dicyclohexylphosphine, and dioctylphosphine; tri-hydrocarbon-substituted phosphines such as trimethylphosphine, triethylphosphine, tripropylphosphine, tributylphosphine, trihexylphosphine, tricyclohexylphosphine, and trioctylphosphine; dialkenylphosphines obtainable by substituting two hydrogen atoms of a monoalkenylphosphine such as vinylphosphine, propenylphosphine, or cyclohexenylphosphine, or phosphine with alkenyl groups; and trialkenylphosphines obtainable by substituting three hydrogen atoms of phosphine with alkenyl groups; and arylphosphines, which include arylalkylphosphines such as benzylphosphine, phenylethylphosphine, and phenylpropylphosphine; diarylalkylphosphines or aryldialkylphosphines obtainable by substituting three hydrogen atoms of phosphine with aryl groups or alkenyl groups; phenylphosphine, tolylphosphine, dimethylphenylphosphine, trimethylphenylphosphine, ethylphenylphosphine, propylphenylphosphine, biphenylphosphine, naphthylphosphine, methylnaphthylphosphine, anthracenylphosphine, phenanthrylphosphine; di(alkylaryl)phosphines obtainable by substituting two hydrogen atoms of phosphine with alkylaryl groups; and tri(alkylaryl)phosphines obtainable by substituting three hydrogen atoms of phosphine with alkylaryl groups.

As specific examples of thioethers, the above sulfides can be given.

$Q^1$ and $Q^2$ have a structure represented by the formula (2) or (3), and $Q^1$ and $Q^2$ may be different or the same.

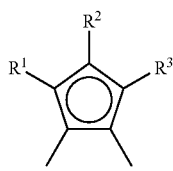

(2)

wherein $R^1$ to $R^3$ are a hydrogen atom, halogen atom, hydrocarbon group with 1 to 20 carbon atoms., halogen-containing hydrocarbon group with 1 to 4 carbon atoms, silicon-containing group, or hetero-atom-containing group.

As the halogen atom in the formula (2), a chlorine atom, fluorine atom, bromine atom, and iodine atom can be given.

As specific examples of the hydrocarbon group having 1 to 20 carbon atoms, alkyl groups such as a methyl group, ethyl group, propyl group, isopropyl group, butyl group, hexyl group, cyclohexyl group, and octyl group; alkenyl groups such as a vinyl group, propenyl group, and cyclohexenyl group; arylalkyl groups such as a benzyl group, phenylethyl group, and phenylpropyl group; and aryl groups such as a phenyl group, tolyl group, dimethylphenyl group, trimethylphenyl group, ethylphenyl group, propylphenyl group, biphenyl group, naphthyl group, methylnaphthyl group, anthracenyl group, and phenanthryl group can be given.

Examples of the halogen-containing hydrocarbon group having 1 to 4 carbon atoms include a chloromethyl group, bromomethyl group, bromoethyl group, p-fluorophenyl group, p-fluorophenylmethyl group, 3,5-difluorophenyl group, pentachlorophenyl group, 3,4,5-trifluorophenyl group, pentafluorophenyl group, and 3,5-bis(trifluoromethyl) phenyl group.

As specific examples of the silicon-containing group, mono-hydrocarbon-substituted silyl groups such as a methylsilyl group and phenylsilyl group; di-hydrocarbon-substituted silyl groups such as a dimethylsilyl group and diphenylsilyl group; tri-hydrocarbon-substituted silyl groups such as a trimethylsilyl group, triethylsilyl group, tripropylsilyl group, dimethyl(t-butyl)silyl group, tricyclohexylsilyl group, triphenylsilyl group, dimethylphenylsilyl group, methyldiphenylsilyl group, tritolylsilyl group, and trinaphthylsilyl group; hydrocarbon-substituted silyl ether groups such as a trimethyl silyl ether group; silicon-substituted alkyl groups such as a trimethylsilylmethyl group; silicon-substituted aryl groups such as a trimethylsilylphenyl group; dimethylhydrosilyl group, methyldihydrosilyl group, and the like can be given.

As specific examples of the hetero-atom-containing group, a diphenylphosphino group, dimethylboryl group, diphenylboryl group, and dimethylarsenyl group can be given.

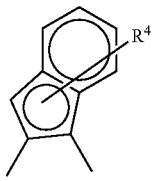

(3)

wherein $R^4$ is a hydrogen atom or a hydrocarbon group with 1 to 20 carbon atoms.

In the formula (3), $R^4$ bonds to the 3 to 7 positions of the indenyl group. As specific examples of the hydrocarbon group having 1 to 20 carbon atoms, alkyl groups such as a methyl group, ethyl group, propyl group, butyl group, hexyl group, cyclohexyl group, and octyl group; alkenyl groups such as a vinyl group, propenyl group, and cyclohexenyl group; arylalkyl groups such as a benzyl group, phenylethyl group, and phenylpropyl group; and aryl groups such as a phenyl group, tolyl group, dimethylphenyl group, trimethylphenyl group, ethylphenyl group, propylphenyl group, biphenyl group, naphthyl group, methylnaphthyl group, anthracenyl group, and phenanthryl group can be given.

Specific examples of the transition metal compound of the formula (1) include (1,1'-Me$_2$Si) (2,2'-PhP)(3-methyl-5-isopropylcyclopentadienyl)$_2$ZrCl$_2$, (1,1'-Me$_2$Si)(2,2'-(i-Pr)$_2$NB)(3,5-diisopropylcyclopentadienyl)(indenyl)ZrCl$_2$, (1,1'-Me$_2$SiSiMe$_2$)(2,2'-(i-Pr)$_2$NB)(indenyl)$_2$ZrCl$_2$, (1,2'-MeB)(2,1'-MeB)(indenyl)$_2$ZrCl$_2$, (1,2'-PhB)(2,1'-PhB)(indenyl)$_2$ZrCl$_2$, (1,2'-MeP)(2,1'-MeP)(indenyl)$_2$ZrCl$_2$, (1,2'-PhP)(2,1'-PhP)(indenyl)$_2$ZrCl$_2$, (1,2'-(i-Pr)$_2$NB)(2,1'-(i-Pr)$_2$ NB)(indenyl)$_2$ZrCl$_2$, (1,2'-MeB)(2,1'-Me$_2$Si)(indenyl)$_2$ ZrCl$_2$, (1,2'-PhB)(2,1'-Me$_2$Si)(indenyl)$_2$ZrCl$_2$, (1,2'-MeP)(2,1'-Me$_2$Si)(indenyl)$_2$ZrCl$_2$, (1,2'-PhP)(2,1'-Me$_2$Si)(indenyl)$_2$ZrCl$_2$, (1,2'-(i-Pr)$_2$NB)(2,1'-Me$_2$Si)(indenyl)$_2$ ZrCl$_2$, (1,2'-MeB)(2,1'-MeB)(indenyl)(cyclopentadienyl)ZrCl$_2$, (1,2'-PhB)(2,1'-PhB)(indenyl)(cyclopentadienyl)ZrCl$_2$, (1,2'-MeP)(2,1'-MeP)(indenyl)(cyclopentadienyl)ZrCl$_2$, (1,2'-PhP)(2,1'-PhP)(indenyl)(cyclopentadienyl)ZrCl$_2$, (1,2'-(i-Pr)$_2$NB)(2,1'-(i-Pr)$_2$NB)(indenyl)(cyclopentadienyl)ZrCl$_2$, (1,2'-Me$_2$Si)(2,1'-MeB)(indenyl)(cyclopentadienyl)ZrCl$_2$, (1,2'-Me$_2$Si)(2,1'-PhB)(indenyl)(cyclopentadienyl)ZrCl$_2$, (1,2'-Me$_2$Si)(2,1'-MeP)(indenyl)(cyclopentadienyl)ZrCl$_2$, (1,2'-Me$_2$Si)(2,1'-PhP)(indenyl)(cyclopentadienyl)ZrCl$_2$, and (1,2'-Me$_2$Si)(2,1'-(i-Pr)$_2$NB)(indenyl)(cyclopentadienyl)ZrCl$_2$.

Of these, (1,1'-Me$_2$Si)(2,2'-PhP)(3-methyl-5-iso-propyl-cyclopentadienyl)$_2$ZrCl$_2$, (1,1'-Me$_2$Si)(2,2'-(i-Pr)$_2$NB)(3,5-diisopropylcyclopentadienyl)(indenyl)ZrCl$_2$, (1,1'-

Me$_2$SiSiMe$_2$)(2,2'-(i-Pr)$_2$NB)(indenyl)$_2$ZrCl$_2$, and (1,2'-PhP)(2,1'-Me$_2$Si)(indenyl)$_2$ZrCl$_2$ are preferable.

The transition metal compounds further include, but are not limited to, those of the above-described compounds in which the zirconium is substituted with titanium or hafnium. Moreover, similar compounds of metal elements of other groups or a lanthanoid can be used.

The transition metal compound of formula (1) can be synthesized by a method such as that described in J. Organomet. Chem, vol. 369, page 359 (1989), for example. Specifically, a reaction of a corresponding substituted-cycloalkenyl anion with the halide compound of the above-mentioned M is preferable.

(2) Olefin Polymerization Catalyst

The transition metal compound of the invention can be used as a catalyst for olefin polymerization. This catalyst preferably comprises, in addition to the transition metal compound (A), an activating co-catalyst (B) and, as required, an organoaluminum compound (C).

As the activating co-catalyst (B), a compound-which can react with the component (A) or a compound derived therefrom to form an ionic complex, clay, clay mineral, or an ion-exchange layered compound can be used.

As the compound that reacts with the component (A) or a compound derived therefrom to form an ionic complex, the following compounds can be given as preferable examples in view of high polymerization activity and low catalyst cost.

(B-1) An Ionic Compound which Reacts with the Transition Metal Compound (A) to Form an Ionic Complex
(B-2) Aluminoxane
(B-3) Lewis Acid As the component (B-1), although any ionic compounds that reacts with the transition metal compound (A) to form an ionic complex can be used, compounds represented by the following formulas (7) or (8) are particularly preferable due to efficient formation of polymerization active sites.

([L$^1$-R$^{11}$]$^{h+}$)$_a$([Z]$^-$)$_b$     (7)

([L$^2$]h$^+$)$_a$([Z]$^-$)$_b$     (8)

In the formulas, L$^1$ represents a Lewis base. As specific examples of L$^1$, amines such as ammonia, methylamine, aniline, dimethylamine, diethylamine, N-methylaniline, diphenylamine, N,N-dimethylaniline, trimethylamine, triethylamine, tri-n-butylamine, methyldiphenylamine, pyridine, p-bromo-N,N-dimethylaniline, and p-nitro-N,N-dimethylaniline; phosphines such as triethylphosphine, triphenylphosphine, and diphenylphosphine; thioethers such as tetrahydrothiophene; esters such as ethyl benzoate; and nitriles such as acetonitrile and benzonitrile can be given.

R$^{11}$ represents a hydrogen atom, an alkyl group having 1 to 20 carbon atoms or an aryl, alkylaryl, or arylalkyl group having 6 to 20 carbon atoms. As specific examples of R$^{11}$, hydrogen, a methyl group, ethyl group, benzyl group, and trityl group can be given.

[Z]$^-$ is a non-coordinating anion and includes the following [Z$^1$]$^-$ or [Z$^2$]$^-$.

[Z$^1$]$^-$ is an anion in which a plurality of groups bond to an element and is shown by the formula [M$^3$G$^1$G$^2$ . . . G$^f$], wherein M$^3$ indicates an element of the groups 5 to 15, preferably groups 13 to 15, of the periodic table. As specific examples of M$^3$, B, Al, Si, P, As, Sb, and the like can be given, with preferable elements being B and Al.

G$^1$ to G$^f$ individually represents a hydrogen atom, halogen atom, alkyl group having 1 to 20 carbon atoms, dialkylamino group having 2 to 40 carbon atoms, alkoxy group having 1 to 20 carbon atoms, aryl group having 6 to 20 carbon atoms, aryloxy group having 6 to 20 carbon atoms, alkylaryl group having 7 to 40 carbon atoms, arylalkyl group having 7 to 40 carbon atoms, halogen-substituted hydrocarbon group having 1 to 20 carbon atoms, acyloxy group having 1 to 20 carbon atoms, organic metalloid group, or hetero-atom-containing hydrocarbon group having 2 to 20 carbon atoms. Two or more of G$^1$ to G$^f$ may form a ring together. f is an integer equivalent to [(atomic valence of central metal M$^3$)+1].

Specific examples of G$^1$ to G$^f$ include, a dimethylamino group, diethylamino group as the dialkylamino group; methoxy group, ethoxy group, n-butoxy group, and phenoxy group as the alkoxy group or aryloxy group; a methyl group, ethyl group, n-propyl group, isopropyl group, n-butyl group, isobutyl group, n-octyl group, n-eicosyl group, phenyl group, p-tolyl group, benzyl group, 4-t-butylphenyl group, and 3,5-dimethyl phenyl group as the hydrocarbon group; fluorine, chlorine, bromine, and iodine as the halogen atom; p-fluorophenyl group, 3,5-difluorophenyl group, pentachlorophenyl group, 3,4,5-trifluorophenyl group, pentafluorophenyl group, 3,5-bis(trifluoromethyl)phenyl group, and bis(trimethylsilyl)methyl group as the hetero-atom-containing hydrocarbon group; pentamethylantimony group, trimethylsilyl group, trimethylgermyl group, diphenylarsine group, dicyclohexylantimony group, and diphenyl boron as the organic metalloid group.

[Z2]$^-$ represents a conjugated base of a Bronsted acid of which a logarithm of an inverse of acid dissociation constant (pKa) is –10 or less, a conjugated base of a combination of the Bronsted acid and a Lewis acid, or a conjugated base generally defined as a super-strong acid. In addition, a Lewis base may be coordinated.

As specific examples, a trifluoromethansulfonic acid anion. (CF$_3$SO$_3$)$^-$, bis(trifluoromethanesulfonyl)methyl anion, bis(trifluoromethanesulfonyl)benzyl anion, bis(trifluoromethanesulfonyl)amide, perchloric acid anion (ClO$_4$)$^-$, trifluoroacetic acid anion (CF$_3$CO$_2$)$^-$, hexafluoroantimony anion (SbF$_6$)$^-$, fluorosulfonic acid anion (FSO$_3$)$^-$, chlorosulfonic acid anion (ClSO$_3$)$^-$, fluorosulfonic acid anion/antimony pentafluoride (FSO$_3$/SbF$_5$)$^-$, fluorosulfonic acid anion/arsenic pentafluoride (FSO$_3$/AsF$_5$)$^-$, and trifluoromethansulfonic acid anion/antimony pentafluoride (CF$_3$SO$_3$/SbF$_5$)$^-$ can be given.

h, which represents an ionic valence of [L$^1$-R$^{11}$] and [L$^2$], is an integer of 1 to 3, a is an integer of 1 or more, and b=(h×a).

In the formula (8), L$^2$ is M$^1$, R$^{12}$R$^{13}$M$^2$, R$^{14}{}_3$C, or R$^{15}$M$^2$, wherein M$^1$ includes elements of the groups 1 to 3, 11 to 13, and 17 of the periodic table and M$^2$ represents an element of the groups 7 to 12 of the periodic table. As specific examples of M$^1$, Li, Na, K, Ag, Cu, Br, I, and I$_3$ can be given and as specific examples of M$^2$, Mn, Fe, Co, Ni, and Zn can be given.

R$^{12}$ and R$^{13}$ individually represent a cyclopentadienyl group, substituted cyclopentadienyl group, indenyl group, substituted indenyl group, fluorenyl group, or substituted fluorenyl group. As specific examples of R$^{12}$ and R$^{13}$, a cyclopentadienyl group, methylcyclopentadienyl group, ethylcyclopentadienyl group, and pentamethylcyclopentadienyl group can be given.

R$^{14}$ represents an alkyl group, aryl group, alkylaryl group, or arylalkyl group having 1 to 20 carbon atoms. As specific examples of R$^{14}$, a phenyl group, p-tolyl group, and p-methoxyphenyl group can be given.

R$^{15}$ represents a macrocyclic ligand such as tetraphenylporphyrin and phthalocyanine. As specific examples of R$^{15}$, tetraphenylporphin, phthalocyanine, allyl, and methallyl can be given.

The following compounds can be given as specific examples of the compound of the component (B-1): triethylammonium tetraphenylborate, tri-n-butylammonium tetraphenylborate, trimethylammonium tetraphenylborate, tetraethylammonium tetraphenylborate, methyl(tri-n-butyl)ammonium tetraphenylborate, benzyl(tri-n-butyl)ammonium tetraphenylborate, dimethyldiphenylammonium tetraphenylborate, triphenyl(methyl)ammonium tetraphenylborate, trimethylanilinium tetraphenylborate, methylpyridinium tetraphenylborate, benzylpyridinium tetraphenylborate, (methyl)(2-cyanopyridinium)tetraphenylborate, triethylammonium tetrakis(pentafluorophenyl)borate, tri-n-butylammonium tetrakis(pentafluorophenyl)borate, triphenylammonium tetrakis(pentafluorophenyl)borate, tetra-n-butylammonium tetrakis(pentafluorophenyl)borate, tetraethylammonium tetrakis(pentafluorophenyl)borate, benzyl(tri-n-butyl)ammonium tetrakis(pentafluorophenyl)borate, methyldiphenylammonium tetrakis(pentafluorophenyl)borate, triphenyl(methyl)ammonium tetrakis(pentafluorophenyl)borate, methylanilinium tetrakis(pentafluorophenyl)borate, dimethylanilinium tetrakis(pentafluorophenyl)borate, trimethylanilinium tetrakis(pentafluorophenyl)borate, methylpyridinium tetrakis(pentafluorophenyl)borate, benzylpyridinium tetrakis(pentafluorophenyl)borate, methyl(2-cyanopyridinium)tetrakis(pentafluorophenyl)borate, benzyl(2-cyanopyridinium)tetrakis(pentafluorophenyl)borate, methyl(4-cyanopyridinium)tetrakis(pentafluorophenyl)borate, triphenylphosphonium tetrakis(pentafluorophenyl)borate, dimethylanilinium tetrakis[bis(3,5-ditrifluoromethyl)phenyl]borate, ferrocenium tetraphenyl borate, silver tetraphenyl borate, trityl tetraphenyl borate, tetraphenylporphyrinmanganese tetraphenyl borate, ferrocenium tetrakis(pentafluorophenyl)borate, (1,1'-dimethylferrocenium)tetrakis(pentafluorophenyl)borate, decamethylferrocenium tetrakis(pentafluorophenyl)borate, silver tetrakis(pentafluorophenyl)borate, trityl tetrakis(pentafluorophenyl)borate, lithium tetrakis(pentafluorophenyl)borate, sodium tetrakis(pentafluorophenyl)borate, tetraphenylporphyrinmanganese tetrakis(pentafluorophenyl)borate, silver tetrafluoroborate, silver hexafluorophosphate, silver hexafluoroarsenate, silver perchlorate, silver trifluoroacetate, and silver trifluoromethanesulfonate.

These ionic compounds of the component (B-1) may be used either individually or in combination of two or more.

As the aluminoxane of the component (B-2), linear aluminoxanes shown by the formula (9) and cyclic aluminoxanes shown by the formula (10) can be given,

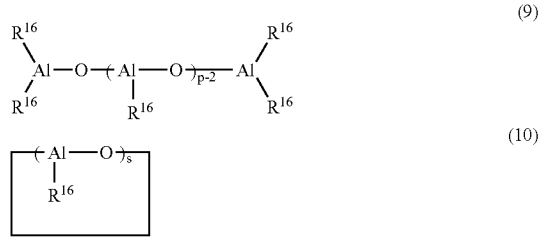

wherein $R^{16}$ individually represents an alkyl group having 1 to 20, preferably 1 to 8 carbon atoms, with different $R^{16}$s being either the same or different, and p is an integer satisfying an inequality formula of $2<p\leq 40$, and s is an integer satisfying an inequality formula of $1<s\leq 50$.

As specific examples, aluminoxanes such as methylaluminoxane, ethylaluminoxane, and isobutylaluminoxane can be given.

As the method for producing the aluminoxanes, a method of causing alkylaluminum to come in contact with a condensing agent such as water can be given. As to the details of the process, known methods of reaction may be followed without specific limitations.

For example, a method of dissolving an organoaluminum compound in an organic solvent and causing the solution to come in contact with water, a method of adding an organoaluminum compound at the start of polymerization and adding water later, a method of causing crystal water contained in a metal salt and the like or adsorbed water contained in an inorganic or organic compound to react with an organoaluminum compound, and a method of reacting trialkylaluminum with tetraalkyldialuminoxane and reacting the resulting reaction product with water can be given.

The aluminoxane may be either soluble or insoluble in toluene. These aluminoxanes can be used either individually or in combination of two or more.

There are no specific limitations to the Lewis acid of the component (B-3). Either an organic compound or a solid inorganic compound may be used.

As the organic compound, a boron compound, an aluminum compound, and the like are preferably used due to their capability of efficiently forming active sites.

As examples of the boron compound, triphenylboron, tris(pentafluorophenyl)boron, tris[3,5-bis(trifluoromethyl)phenyl]boron, tris[(4-fluoromethyl)phenyl]boron, trimethylboron, triethylboron, tri-n-butylboron, tris(fluoromethyl)boron, tris(pentafluoroethyl)boron, tris(nonafluorobutyl)boron, tris(2,4,6-trifluorophenyl)boron, tris(3,5-difluoro)boron, tris[3,5-bis(trifluoromethyl)phenyl]boron, bis(pentafluorophenyl)fluoroboron, diphenylfluoroboron, bis(pentafluorophenyl)chloroboron, dimethylfluoroboron, diethylfluoroboron, di-n-butylfluoroboron, pentafluorophenyldifluoroboron, phenyldifluoroboron, pentafluorophenyldichloroboron, methyldifluoroboron, ethyldifluoroboron, and n-butyldifluoroboron can be given.

As examples of the organoaluminum compound, methyl bis(2,6-di-t-butyl-4-methylphenoxy)aluminum, methyl(1,1-bis-2-naphthoxy)aluminum, and the like can be given.

As the solid inorganic compound, a magnesium compound, an aluminum compound, and the like are preferably used due to their capability of efficiently forming active sites.

As the magnesium compound, for example, magnesium chloride, diethoxymagnesium, and the like can be used. As the aluminum compounds, aluminum oxide, aluminum chloride, and the like can be used.

These Lewis acids can be used either individually or in combination of two or more.

In addition to the components (B-1) to (B-3), which are compounds that can react with the component (A) or a compound derived therefrom to form an ionic complex, clay, clay mineral, or an ion-exchange layered compound can be suitably used as the component (B).

Clay is an aggregate of fine hydrous silicate mineral and exhibits plasticity when kneaded with an appropriate amount of water. A formed clay product exhibits rigidity when dried and can be sintered if burnt at a high temperature. Clay mineral is hydrous silicate, which is a major component of clay.

Either clay or clay mineral may be used for preparing the olefin polymerization catalyst component. These may be either a naturally occurring material or synthesized material.

As the clay and clay mineral, clay called bentonite due to a small content of montmorillonite, kibushi clay comprising montmorillonite and many other components, gaerome clay, fibrous sepiolite, palygorskite, noncrystalline or low crystalline allophane, imogolite, and the like can be given.

In addition, phyllosilicic acids such as phyllosilicic acid and phyllosilicate can be mentioned. Phyllosilicate includes montmorillonite, saponite, and hectorite belonging to the smectite group, illite and sericite belonging to the mica group, mixed layer minerals of the smectite group and mica group or the mica group and vermiculite group, and the like as naturally occurring materials. As the synthetic material, fluorotetrasilicic mica, laponite, smecton, and the like can be given.

The ion-exchange layered compound is a compound having a crystal structure in which the planes formed by ionic bonds and the like are stacked in parallel by weak bonding strength. Ions included therein are exchangeable. Some of the above-mentioned clay minerals are ion-exchange layered compounds.

As the ion-exchange layered compound, α-Zr(HPO$_4$)$_2$, γ-Zr(HPO$_4$)$_2$, α-Ti(HPO$_4$)$_2$, γ-Ti(HPO$_4$)$_2$, and the like can be given.

The volume average particle diameter of these components (B) is preferably 10 μm or less, and more preferably 3 μm or less.

In general, an aggregate of particles has a particle diameter distribution. In the case of component (B), the proportion of particles having a volume average particle diameter of 10 μm or less and a volume particle diameter of 3.0 μm or less is preferably 10 wt % or more. The component (B) of which the proportion of particles having a volume average particle diameter of 10 μm or less and a volume particle diameter of 1.5 μm or less is 10 wt % or more is particularly preferable.

As the method for measuring the volume average particle diameter and particle size distribution, a method of using an instrument for measuring particle size by laser light transmission (e.g. "CIS-1" manufactured by GALAI Production Ltd.) can be given, for example.

These components (B) may be pretreated with an organosilicon compound or organoaluminum compound.

Among the above-mentioned components (B), a compound having high capability of adsorbing quaternary ammonium salts (which include, but are not limited to quaternary alkylammonium salt, quaternary arylammonium salt, quaternary arylalkylammonium salt, quaternary benzylammonium salt, and hetero aromatic ammonium salt) or reacting with clay and the like to produce an intercalation compound is preferable. For example, clay or clay mineral, specifically, phyllosilicic acids are preferable, and a more preferable component (B) is smectite, with a particularly preferable clay mineral being montmorillonite. As a synthetic compound, fluorotetrasilicic mica is preferable.

The ratio of the transition metal compound (A) to the activating co-catalyst (B) in the catalyst for polymerization of the invention, in terms of molar ratio, is preferably 10:1 to 1:100, and more preferably 2:1 to 1:10, in the case when the compound (B-1) is used as the component (B). The ratio outside of this range is not practical because the catalyst cost per unit weight of the polymer increases.

When the compound (B-2) is used as the component (B), the molar ratio is preferably 1:1 to 1:1,000,000, and more preferably 1:10 to 1:10,000. The ratio outside of this range is not practical because the catalyst cost per unit weight of the polymer increases.

When the compound (B-3) is used as the component (B), the molar ratio is preferably 10:1 to 1:2,000, more preferably 5:1 to 1:1,000, and still more preferably 2:1 to 1:500. The ratio outside of this range is not practical because the catalyst cost per unit weight of the polymer increases.

As the catalyst component (B), the components (B-1), (B-2), (B-3), and the like may be used either individually or in combination of two or more.

When clay, clay mineral, or an ion-exchange compound is used as the component (B), the ratio of the component (A) to component (B), in terms of the amount of the transition metal complex of the component (A) relative to a unit weight (g) of the clay and the like of the component (B), is 0.1 to 1,000 μmol, and preferably 1 to 100 μmol.

The polymerization catalyst of the invention may optionally contain an organoaluminum compound (C).

As the organoaluminum compound of the component (C), compounds of the following formula (11) can be used, $$R^{17}{}_{v}AlX^{1}{}_{3-v} \qquad (11)$$

wherein $R^{17}$ represents an alkyl group having 1 to 10 carbon atoms, $X^1$ represents a hydrogen atom, alkoxy group having 1 to 20 carbon atoms, aryl group having 6 to 20 carbon atoms, or halogen atom, and v is a real number of 1 to 3.

As specific examples of the compound shown by the formula (11), trimethylaluminum, triethylaluminum, triisopropylaluminum, triisobutylaluminum, dimethylaluminum chloride, diethylaluminum chloride, methylaluminum dichloride, ethylaluminum dichloride, dimethylaluminum fluoride, diisobutylaluminum hydride, diethylaluminum hydride, and ethylaluminum sesquichloride can be given.

These organoaluminum compounds can be used either individually or in combination of two or more.

The ratio of the catalyst component (A) to the catalyst component (C), in terms of the molar ratio, is preferably 1:1 to 1:10,000, more preferably 1:5 to 1:2,000, and still more preferably 1:10 to 1:1,000. The polymerization activity per unit amount of the transition metal can be increased by using the catalyst component (C). However, too great an amount of the component (c), particularly, an amount exceeding the above range leads to waste of the organoaluminum compound and an increase of the amount of the organoaluminum compound remaining in the polymer. Too small an amount, on the other hand, may be undesirable because of insufficient catalytic activity.

In the invention, when or after the components are caused to come into contact, polymers such as polyethylene and polypropylene, or inorganic oxide compounds such as silica and alumina may be present together or caused to come into contact.

When the catalyst is carried on a carrier, a polymer is preferably used as the carrier. The carrier polymer has a particle diameter of 1 to 300 μm, preferably from 10 to 200 μm, and more preferably 20 to 100 μm. If the particle diameter is less than 1 μm, fine particles in the polymer increase; if more than 300 μm, large and rough particles in the polymer increase, resulting in a decrease of bulk density and blocking of the hopper in the production process. In this instance, the specific surface area of the carrier is 1 to 1,000 m$^2$/g, and preferably 50 to 500 m$^2$/g, and the pore volume is 0.1 to 5 m$^3$/g, and preferably 0.3 to 3 m$^3$/g.

The contact may be carried out in an inert gas such as nitrogen or in a hydrocarbon such as pentane, hexane, heptane, toluene, and xylene.

The catalyst components can be added or caused to come in contact at a polymerization temperature, as a matter of course, or at a temperature in a range from −30° C. to the boiling point of the solvent, particularly preferably from room temperature to the boiling point of the solvent.

(3) Process for Producing Olefin Polymer

The method for producing olefin polymer of the invention comprises homo or co-polymerizing olefins in the presence of the catalyst for olefin polymerization, which is formed by causing the above-described transition metal compound (A), the activating co-catalyst (B), and optionally the organoaluminum compound (C) to come into contact.

As the organoaluminum compound (C), a compound of the above formula (9) can be used, but preferably a trialkylaluminum compound is used. Particularly preferable compounds are trimethylaluminum and triisobutylaluminum.

In the method for producing olefin polymer of the invention, the organoaluminum compound of the component (C) may be previously caused to come in contact with the component (A) and/or component (B). It is also possible to charge the component (C) into the reactor, followed by contact with the component (A) and component (B).

According to the method for producing olefin polymer of the invention, homo polymerization of an olefin or co-polymerization of an olefin with another olefin and/or another monomer (i.e. copolymerization of different types of olefins, copolymerization of an olefin with another monomer, or copolymerization of different types of olefins and another monomer) can be suitably carried out using the above-described catalyst for olefin polymerization.

Although there are no specific limitations to the olefins, α-olefins having 2 to 20 carbon atoms are preferably used. As specific examples, α-olefins such as ethylene, propylene, 1-butene, 1-pentene, 1-hexene, 1-heptene, 1-octene, 1-nonene, 1-decene, 4-phenyl-1-butene, 6-phenyl-1-hexene, 3-methyl-1-butene, 1-pentene, 3-methyl-1-pentene, 4-methyl-1-hexene, 5-methyl-1-hexene, 3,3-dimethyl-1-pentene, 3,4-dimethyl-1-pentene, 4,4-dimethyl-1-pentene, and vinylcyclohexane; dienes such as 1,3-butadiene, 1,4-pentadiene, and 1,5-hexadiene; halogen-substituted α-olefins such as hexafluoropropene, tetrafluoroethylene, 2-fluoropropene, fluoroethylene, 1,1-difluoroethylene, 3-fluoropropene, trifluoroethylene, and 3,4-dichloro-1-butene; cycloolefins such as cyclopentene, cyclohexene, norbornene, 5-methylnorbornene, 5-ethylnorbornene, 5-propylnorbornene, 5,6-dimethylnorbornene, and 5-benzylnorbornene; as styrene compounds, alkylstyrenes such as styrene, p-methylstyrene, p-ethylstyrene, p-propylstyrene, p-isopropylstyrene, p-butylstyrene, p-tert-butylstyrene, p-phenylstyrene, o-methylstyrene, o-ethylstyrene, o-propylstyrene, o-isopropylstyrene, m-methylstyrene, m-ethylstyrene, m-isopropylstyrene, m-butylstyrene, mesitylstyrene, 2,4-dimethylstyrene, 2,5-dimethylstyrene, and 3,5-dimethylstyrene; alkoxystyrenes such as p-methoxystyrene, o-methoxystyrene, and m-methoxystyrene; halogen-containing styrenes such as p-chlorostyrene, m-chlorostyrene, o-chlorostyrene, p-bromostyrene, m-bromostyrene, o-bromostyrene, p-fluorostyrene, m-fluorostyrene, o-fluorostyrene, and o-methyl-p-fluorostyrene; trimethylsilylstyrene, vinylbenzoate, divinylbenzene, and the like can be given.

The afore-mentioned other olefins can also be appropriately selected from these olefins.

The above olefins may be used either individually or in combination of two or more in the invention. When two or more olefins are copolymerized, the above olefins may be arbitrarily combined.

In the invention, the above-mentioned olefins may be copolymerized with other monomers. As examples of the other monomers that can be used here, linear diolefins such as butadiene, isoprene, 1,4-pentadiene, and 1,5-hexadiene; polycycloolefins such as norbornene, 1,4,5,8-dimethano-1,2,3,4,4a,5,8,8a-octahydronaphthalene, and 2-norbornene; cyclodiolefins such as norbornadiene, 5-ethylidenenorbornene, 5-vinylnorbornene, and dicyclopentadiene; and unsaturated esters such as ethyl acrylate and methyl methacrylate can be given.

In the invention, propylene is particularly preferable as the olefin. There are no specific limitations to the method for polymerizing olefins in the invention. Any optional polymerization method such as a slurry polymerization method, solution polymerization method, vapor-phase polymerization method, mass polymerization method, and suspension polymerization method can be used.

When a polymerization solvent is used, hydrocarbons and halogenated hydrocarbons such as benzene, toluene, xylene, n-hexane, n-heptane, cyclohexane, methylene chloride, chloroform, 1,2-dichloroethane, and chlorobenzene can be given as the solvent. These solvents can be used either individually or in combination of two or more. In addition, monomers used for the polymerization can also be used as the solvent according to the type of monomer.

The amount of the catalyst used in the polymerization reaction, in terms of the amount of the component (A) per 1 l of a solvent, is selected from a range usually from 0.5 to 100 μmol, and preferably from 2 to 25 μmol from the viewpoint of polymerization activity and reaction efficiency.

The polymerization is carried out usually under atmospheric pressure to 2,000 kg/cm$^2$·G. The reaction temperature is usually from −50° C. to 250° C. As the method for regulating the molecular weight of the polymer, selection of catalyst components, the amount used, polymerization temperature, introduction of hydrogen, and the like can be given.

In the polymerization of olefins according to the invention, a preliminary polymerization can be carried out using the above-mentioned catalyst. The preliminary polymerization comprises causing a small amount of olefins to come in contact with a solid catalyst component. The reaction temperature of the preliminary polymerization is from −20 to 100° C., preferably from −10 to 70° C., and particularly preferably from 0 to 50° C.

Although inert hydrocarbons, aliphatic hydrocarbons, aromatic hydrocarbons, and monomers can be used as the solvent in the preliminary polymerization, the aliphatic hydrocarbons are particularly preferable. The preliminary polymerization may be carried out without using a solvent.

It is preferable that the preliminary polymerization product has an intrinsic viscosity [η] (measurement in decalin at 135° C.) of 0.2 dL/g or more, and preferably 0.5 dL/g or more. The preliminary polymerization conditions are preferably adjusted so that 1 to 10,000 g, preferably 10 to 1,000 g of a preliminary polymerization product can be obtained per one mmol of the transition metal component in the catalyst.

EXAMPLES

The invention will now be described in more detail by way of examples. The following embodiment should not be construed as limiting the invention.

<Transition Metal Compound>

Example 1

Synthesis of (1,1'-Me$_2$Si)(2,2'-PhP)(3-methyl-5-iso-propylcyclopentadienyl)$_2$ zirconium dichloride [formula (12)]

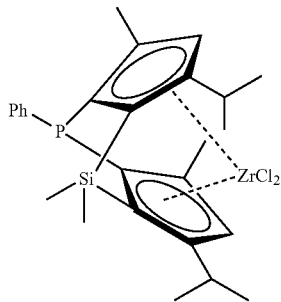

(12)

(a) Synthesis of bis(2-methyl-4-iso-propylcyclopentadienyl)phenylphosphine 1-methyl-3-iso-propylcyclopentadiene was synthesized by reducing 3,6,6-trimethylfulvene.

1.9 g (14.8 mmol) of lithium salt of 1-methyl-3-iso-propylcyclopentadiene was dissolved in 30 ml of dehydrated tetrahydrofuran in a nitrogen stream. The solution was cooled to −78° C.

1.0 ml (7.4 mmol) of dichlorophenylphosphine was added to the solution, and the temperature was increased to room temperature, followed by stirring for eight hours. The solvent was evaporated under reduced pressure and the residue was extracted with hexane to obtain bis(2-methyl-4-iso-propylcyclopentadienyl)phenylphosphine. 2.57 g of the product was obtained at a yield of 94.0%.

(b) Synthesis of (1,1'-Me$_2$Si)(2,2'-PhP)(3-methyl-5-iso-propylcyclopentadiene)$_2$ 2.6 g (7.33 mmol) of bis(2-methyl-4-iso-propylcyclopentadienyl)phenylphosphine was dissolved in 30 ml of dehydrated ether in a nitrogen stream. The solution was cooled to −78° C. After the addition of 10.3 ml of a solution of n-butyllithium in hexane (16.2 mmol, 1.57 M), the mixture was stirred for eight hours at room temperature. The solvent was evaporated under reduced pressure and the residue was washed with hexane to obtain a dilithium salt of bis(2-methyl-4-iso-propylcyclopentadienyl)phenylphosphine. 1.8 g of the product was obtained at a yield of 67.8%.

1.0 g (2.7 mmol) of the dilithium salt was dissolved in 20 ml of dehydrated tetrahydrofuran in a nitrogen stream. The solution was cooled to −78° C. 0.33 ml (2.7 mmol) of dichlorodimethylsilane was added to the solution, and the temperature was increased to room temperature, followed by stirring for eight hours. The solvent was evaporated under reduced pressure and the residue was extracted with hexane/dichloromethane to obtain (1,1'-Me$_2$Si)(2,2'-PhP)(3-methyl-5-iso-propylcyclopentadiene)$_2$.

This compound was used for the following reaction without further purification. 1.03 g of the product was obtained at a yield of 91.6%.

(c) Synthesis of (1,1'-Me$_2$Si)(2,2'-PhP)(3-methyl-5-iso-propylcyclopentadienyl)$_2$ zirconium dichloride 1.03 g (2.53 mmol) of (1,1'-Me$_2$Si)(2,2'-PhP)(3-methyl-5-iso-propylcyclopentadiene)$_2$ was dissolved in 20 ml of dehydrated ether in a nitrogen stream. The solution was cooled to −78° C.

3.5 ml (5.49 mmol, 1.57 M) of a solution of n-butyllithium in hexane was added to the solution, and the temperature was increased to room temperature, followed by stirring for eight hours.

The solvent was evaporated under reduced pressure and the residue was washed with hexane to obtain a dilithium salt of (1,1'-Me$_2$Si)(2,2'-PhP)(3-methyl-5-iso-propylcyclopentadiene)$_2$. 0.53 g (1.14 mmol) of the product was obtained at a yield of 44.9%.

The dilithium salt was suspended in 3 ml of dehydrated toluene in a nitrogen stream and cooled to −78° C. 0.26 g (1.12 mmol) of zirconium tetrachloride toluene suspension was added to the above suspension, and the temperature was increased to room temperature, followed by stirring for eight hours.

The solvent was evaporated under reduced pressure and the residue was extracted with dehydrated dichloromethane and recrystallized by dichloromethane/hexane to obtain (1,1'-Me$_2$Si)(2,2'-PhP)(3-methyl-5-iso-propylcyclopentadienyl)$_2$ zirconium dichloride as a white powder. 0.12 g of the product was obtained at a yield of 18.9%.

$^1$H-NMR(CDCl$_3$) spectrum was −0.50 (s, 3H), 0.50 (s, 3H), 1.04 (d, 6H), 1.30 (d, 6H), 2.33(s, 6H), 2.82(m, 2H), 6.28(2H), 7.28-7.67 (m, 5H).

The $^1$H-NMR spectrum was measured using a 90 MHz NMR analyzer manufactured by JEOL Ltd.

Example 2

Synthesis of (1,1'-Me$_2$Si)(2,2'-(i-Pr)$_2$NB)(3,5-diisopropylcyclopentadienyl)(indenyl)zirconium dichloride [formula (13)]

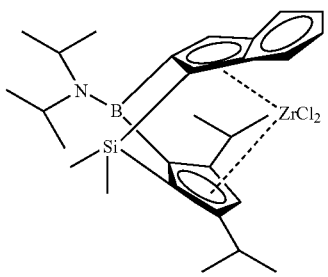

(13)

(a) Synthesis of (2-indenyl)(diisopropylamino)chloroborane 2-bromoindene was synthesized from 2-bromo-1-indanol Bromomagnesium indene was prepared from 10.0 g (51.3 mmol) of 2-bromoindene and 5 g of magnesium in a nitrogen stream. The reaction product was reacted with 6.5 ml of trimethylchlorosilane to obtain 7.14 g (37.9 mmol) of 2-trimethylsilylindene as a colorless oily product.

7.14 g of 2-trimethylsilyl indene was dissolved in 20 ml of dichloromethane. 38.0 ml of boron trichloride (1.0 M, dichloromethane solution) was added thereto at 0° C. and the mixture was stirred for 3 hours at room temperature.

The solvent was evaporated to obtain 7.1 g (36.1 mmol) of (2-indenyl)dichloroborane as a pale yellow solid.

This solid was dissolved in 50 ml of hexane. 10 ml of a solution of 10.1 ml (72.2 mmol) of diisopropylamine in hexane was dropped into the solution at 0° C.

After the dropping, the mixture was heated for two hours while refluxing to filter precipitate by filteration. The solvent of filterate was evaporated under reduced pressure to obtain an oily product, which was distilled under reduced pressure (140° C./90 torr) to obtain 6.42 g (24.5 mmol) of (2-indenyl)(diisopropylamino)chloroborane as a colorless solid.

$^1$H-NMR(CDCl$_3$) spectrum of this compound was –0.50(s, 3H), 0.50(s, 3H), 1.04(d, 6H), 1.30(d, 6H), 2.33(s, 6H), 2.82 (m, 2H), 6.28(2H), 7.28-7.67(m, 5H).

(b) Synthesis of (1,1'-Me$_2$Si)(2,2'-(i-Pr)$_2$NB)(3,5-diisopropylcyclopentadiene)(indene)

2.38 g (15.8 mmol) of 1,3-diisopropylcyclopentadiene was dissolved in 15 ml of toluene and 15 ml of hexane in a nitrogen stream. 11.1 ml of n-butyl lithium (1.56 M hexane solution) was dropped into the solution at 0° C., and the mixture was stirred for eight hours at room temperature.

White precipitate was filtered and dried under reduced pressure to obtain 1.91 g (12.2 mmol) of 1,3-diisopropylcyclopentadienyllithium.

3.20 g (12.2 mmol) of (2-indenyl)(diisopropylamino)chloroborane was dissolved in 20 ml of tetrahydrofuran. The solution was dropped into 20 ml of a solution of 1.91 g of 1,3-diisopropylcyclopentadienyllithium in tetrahydrofuran.

After stirring at room temperature for four hours, the solvent was evaporated and the residue was extracted with 50 ml of hexane to obtain 4.36 g (11.6 mmol) of (3,5-diisopropylcyclopentadienyl)(2-indenyl)(diisopropylamino)borane as a pale yellow solid.

Lithium diisopropylamide was prepared from 3.3 ml (23.5 mmol) of diisopropylamine and 15.0 ml of n-butyl lithium (1.56 M, hexane solution) in 50 ml of tetrahydrofuran.

4.36 g (11.6 mmol) of (3,5-diisopropylcyclopentadienyl)(2-indenyl)(diisopropylamino)borane was dissolved in 30 ml of tetrahydrofuran. The previously prepared lithium diisopropylamide was dropped into the solution at 0° C.

After the dropping, the mixture was stirred at room temperature for two hours. 1.4 ml of dimethyldichlorosilane was dropped into the reaction mixture at 0° C. and the mixture was stirred at room temperature for two hours. The solvent was evaporated and the residue was extracted with 30 ml of hexane. Hexane was evaporated under reduced pressure to obtain 2.44 g (5.65 mmol) of (1,1'-Me$_2$Si)(2,2'-(i-Pr)$_2$NB)(3,5-diisopropylcyclopentadiene)(indene) as a white solid.

(c) Synthesis of (1,1'-Me$_2$Si)(2,2'-(i-Pr)$_2$NB)(3,5-diisopropylcyclopentadienyl)(indenyl)zirconium dichloride 2.44 g (5.65 mmol) of (1,1'-Me$_2$Si)(2,2'-(i-Pr)$_2$NB)(3,5-diisopropylcyclopentadiene)(indene) was dissolved in 30 ml of ether and 7.2 ml of n-butyllithium (1.56 M, hexane solution) was dropped thereinto at –78° C. The mixture was stirred for eight hours at room temperature.

Precipitate was filtered to obtain 1.81 g (4.2 mmol) of a dilithium salt as a white solid. The dilithium salt was suspended in 20 ml of toluene and a separately prepared suspension of 0.95 g (4.1 mmol) of zirconium tetrachloride in 10 ml of toluene was dropped into the above suspension at 0C.

The resulting mixture was stirred at room temperature overnight. Then, the solvent was evaporated and the residue was extracted with 40 ml of hexane to obtain 0.36 g of (1,1'-Me$_2$Si)(2,2'-(i-Pr)$_2$NB)(3,5-diisopropylcyclopentadienyl)(indenyl)zirconium dichloride as a yellow powder.

1H-NMR(C$_6$D$_6$) spectrum was 0.56(d, 3H), 0.82(d, 3H), 0.95(d, 3H), 1.1-1.3(m, 12H), 1.59(d, 3H), 2.62(septet, 1H), 2.85-3.20(septet, 2H), 3.41(septet, 1H), 5.69(s, 1H), 6.48(s, 1H), 6.6-7.7(m, 4H)

The $^1$H-NMR spectrum was measured using a 90 MHz NMR analyzer manufactured by JEOL Ltd.

Example 3

Synthesis of (1,1'-Me$_2$Si)(2,2'-PhP)bis(indenyl)zirconium dichloride [formula (14)]

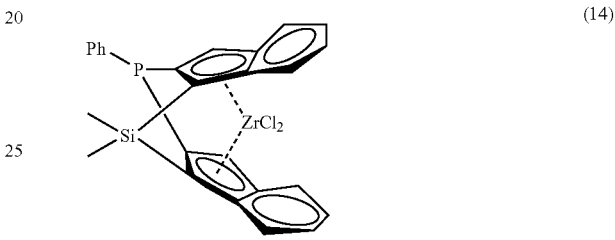

(14)

Dehydrated tetrahydrofuran was added to 10 g (411 mmol) of magnesium in a nitrogen stream. After the addition of 0.2 ml of dibromoethane with stirring to activate magnesium, a solution of 10 g (51.2 mmol) of 2-bromoindene in tetrahydrofuran was dropped thereinto.

After dropping, the mixture was stirred at room temperature for three hours and cooled with ice. After the addition of 3.48 ml (25.5 mmol) of dichlorophenylphosphine, the mixture was stirred at room temperature for eight hours.

The solvent was evaporated under reduced pressure and the residue was extracted with a 1:1 mixture of dichloromethane and hexane. The solvent was evaporated and the residue was washed with hexane to obtain 3.2 g (9.4 mmol) of phenyl-bis(2-indenyl)phosphine.

$^1$H-NMR(CDCl$_3$) spectrum was 3.52(s, 2H), 7.01-7.70(m, 15H).

Next, a solution of 1.58 g (4.6 mmol) of the phenyl-bis(2-indenyl)phosphine in dehydrated tetrahydrofuran was cooled to –78° C. in a nitrogen stream and 6.3 ml (9.7 mmol) of 1.56 M n-butyl lithium solution in hexane was dropped thereinto. The temperature was increased to room temperature and the mixture was stirred for eight hours.

The solvent was evaporated under reduced pressure and the residue was washed with hexane to obtain 1.5 g of dilithium salt (3.5 mmol, THF adduct).

After the addition of dehydrated tetrahydrofuran to the salt and cooling to –78° C., 0.42 ml (3.4 mmol) of dichlorodimethylsilane was added thereto. The mixture was stirred at room temperature for eight hours. The solvent was evaporated under reduced pressure and the residue was extracted with hexane to obtain 1.30 g (3.2 mmol) of 2,2'-phenylphosphono-1,1'-dimethylsilyl-bisindene.

Dehydrated diethyl ether was added to the compound and the mixture was cooled to –78° C. After adding 2.2 ml (3.4 mmol) of a n-butyllithium hexane solution (1.56 M), the temperature was increased to room temperature, followed by stirring for eight hours.

The solvent was evaporated under reduced pressure and the residue was washed with hexane to obtain 1.48 g of a dilithium salt (3.1 mmol, ether adduct).

$^1$H-NMR(THF-$d_8$) spectrum was 0.25(s, 3H), 0.67(s, 3H), 6.35-7.68(m, 10H).

After the addition of dehydrated toluene and cooling to −78° C., 0.72 g (3.1 mmol) of zirconium tetrachloride toluene suspension was added to the salt and the mixture was stirred at room temperature for eight hours. The solvent was evaporated under reduced pressure and the residue was extracted with a dichloromethane/hexane mixture to obtain 0.23 g of (1,1'-Me$_2$Si)(2,2'-PhP)bis(indenyl)zirconium dichloride.

$^1$H-NMR (CDCl$_3$) spectrum was 0.9(s, 3H), 1.21(s, 3H), 6.8-7.6(m, 15H).

Example 4

Synthesis of (1,'1-Me$_2$SiSiMe$_2$)(2,2'-(i-Pr)$_2$NB)(indenyl)$_2$zirconium dichloride [formula (15)]

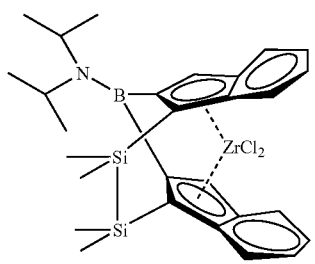

(15)

(a) Synthesis of (1,1'-Me$_2$SiSiMe$_2$)(2,2'-(i-Pr)$_2$NB) bis(indene)

Bromomagnesium indene was prepared by reacting 3.1 g (15.9 mmol) of 2-bromoindene and 1.6 g of magnesium in 50 ml of tetrahydrofuran in a nitrogen stream.

This solution was dropped into a solution of 4.11 g (15.7 mmol) of (2-indenyl)(diisopropylamino)chloroborane in 30 ml of tetrahydrofuran at 0° C. After stirring at room temperature for four hours, the solvent was evaporated and the residue was extracted twice with 40 ml of hexane and 10 ml of dichloromethane to obtain 6.47 g (19.0 mmol) of bis(2-indenyl)(diisopropylamino)borane as a pale yellow solid.

Lithium diisopropylamide was prepared by reacting 3.3 ml (23.5 mmol) of diisopropylamine and 14.8 ml of n-butyl lithium (1.58 M, hexane solution) in 50 ml of tetrahydrofuran.

4.0 g (11.7 mmol) of bis(2-indenyl)(diisopropylamino)borane was dissolved in 30 ml of tetrahydrofuran. A previously prepared lithium diisopropylamide was dropped into the resulting solution at 0° C.

After the dropping, the mixture was stirred at room temperature for two hours to obtain a dark green solution. 2.0 ml of tetramethyldichlorodisilane was dropped into the solution at −78° C. The mixture was stirred at room temperature for two hours. The solvent was evaporated and the residue was extracted twice with 30 ml of hexane. Hexane was evaporated under reduced pressure to obtain 2.61 g (5.7 mmol) of (1,1'-Me$_2$SiSiMe$_2$)(2,2'-(i-Pr)$_2$NB)bis(indene) as a white solid.

(b) Synthesis of (1,1'-Me$_2$SiSiMe$_2$)(2,2'-(i-Pr)$_2$NB) bis(indenyl)zirconium dichloride 1.4 g (3.1 mmol) of (1,1'-Me$_2$SiSiMe$_2$)(2,2'-(i-Pr)$_2$NB)bis (indene) was dissolved in 30 ml of ether and 3.9 ml of n-butyllithium (1.58 M, hexane solution) was dropped thereinto at −78° C. The mixture was stirred for eight hours at room temperature. The solvent was removed under reduced pressure and the resulting solid was washed with 30 ml of hexane to obtain a dilithium salt as a light orange solid.

The dilithium salt was suspended in 20 ml of toluene and a separately prepared suspension of 0.72 g (3.1 mmol) of zirconium tetrachloride in 10 ml of toluene was dropped thereinto at 0° C. The resulting mixture was stirred at room temperature over night. Then, the precipitate was collected by filteration and half of the solvent was removed by condensation. 5 ml of hexane was added to obtain 0.29 g of (1,1'-Me$_2$SiSiMe$_2$)(2,2'-(i-Pr)$_2$NB)(indenyl)$_2$zirconium dichloride as a yellow powder.

$^1$H-NMR(CDCl$_3$) spectrum was 0.50(s, 6H), 0.80(s, 6H), 1.41(d, 6H), 1.48(d, 6H), 4.08(septet, 2H), 6.25(s, 2H), 7.1-7.3(m, 4H), 7.5-7.8(m, 4H).

The $^1$H-NMR spectrum was measured using a 90 MHz NMR analyzer manufactured by JEOL Ltd.

<Olefin Polymer>

Propylene, ethylene, and 1-octadecene was polymerized using the transition metal compound synthesized in Examples 1 to 4.

The following items were evaluated on the obtained polypropylene, and polyethylene.

(1) Pentad Meso Fraction (mmmm)

A proportion of the area occupied by a 21.8 ppm signal of the pentad meso-origin among the total area for 9 signals appearing in 19 to 22 ppm in $^{13}$C-NMR of the polymer was measured using the following instrument under the following conditions.

Instrument: JNM-EX400 NMR analyzer manufactured by JEOL Ltd.

Inspected nucleus: $^{13}$C(100.4 MHz)

Method: $^1$H complete decoupling method

Concentration: about 200 mg/3 ml (6.7×10 kg/m$^3$) (10φ test tube)

Solvent: 90:10 (volume ratio) mixed solvent of 1,2,4-trichlorobenzene and benzene-$d_6$ Temperature: 130° C.

Pulse width: 45°

Pulse repetition time: 4 seconds

Integration: 1000 times.

(2) Melting Point

Apparatus: DSC7 manufactured by Perkin-Elmer Corp.

Rate of temperature increase: 10° C./min

Temperature range: −50 to 150° C.

(3) Intrinsic Viscosity [η]

The viscosity was measured at 135° C. in decaline using an automatic viscometer "VMR-053" manufactured by RIGO CO., LTD.

(4) Molecular Weight (Mw) and Molecular Weight Distribution (Mw/Mn)

Polyethylene-reduced molecular weight was measured by a gel permeation chromatography (GPC) method under the following conditions.

Apparatus: Waters ALC/GPC 150C
Column: GMHHR+H(S)HT×2, manufactured by Tosoh Corp.
Temperature: 145° C.
Solvent: 1,2,4-trichlorobenzene
Flow rate: 1 ml/min Example 5

Propylene Polymerization

A 1 l autoclave, which was heated and dried, was charged with 400 ml of toluene and 1.5 mmol of triisobutylaluminum at room temperature in a nitrogen atmosphere.

The mixture was heated to 50° C. with stirring. Then, 3 mmol of methylaluminoxane and 3 μmol of (1,1'-Me$_2$Si)(2,2'-PhP)(3-methyl-5-iso-propylcyclopentadienyl)$_2$zirconium dichloride obtained in Example 1 were added thereto.

The mixture was polymerized for 30 minutes while controlling pressure at 0.7 MPa with propylene. After the polymerization reaction, the reaction product was charged into methanol. After sufficiently stirring, the resulting precipitate was collected by filtration, sufficiently washed with methanol, and dried to obtain 23.3 g of polypropylene.

The obtained polypropylene had an intrinsic viscosity of 1.21 dl/g and a pentad meso fraction [mmmm] of 5.3%.

The results of evaluation of this polypropylene and the polymers obtained in Examples 6 to 9 and Comparative Examples 1 and 2 described below are shown in Table 1.

TABLE 1

| | Transition metal compound (A) | Monomer | Amount obtained (g) | [η] (dl/g) | [mmmm] (%) |
|---|---|---|---|---|---|
| Example 5 | No. 1 | Propylene | 23.3 | 1.21 | 5.3 |
| Example 6 | No. 2 | Propylene | 45.5 | 1.76 | 10.2 |
| Example 7 | No. 3 | Propylene | 0.8 | 0.22 | — |
| Example 8 | No. 4 | Propylene | 108 | 1.81 | 23.5 |
| Example 9 | No. 1 | Ethylene | 6.7 | 1.02 | — |
| Comparative Example 1 | No. 5 | Propylene | 117 | 0.94 | — |
| Comparative Example 2 | No. 6 | Propylene | 9.93 | 0.24 | — |

No. 1: (1,1'-Me$_2$Si) (2,2'-PhP) (3-methyl-5-iso-propylcyclopentadienyl)$_2$ zirconium dichloride
No. 2: (1,1'-Me$_2$Si) (2,2'-(i-Pr)$_2$NB) (3,5-diisopropylcyclopentadienyl) (indenyl) zirconium dichloride
No. 3: (1,1'-Me$_2$Si) (2,2'-PhP)bis(indenyl)zirconium dichloride
No. 4: (1,1'-Me$_2$SiSiMe$_2$) (2,2'-(i-Pr)$_2$NB) (indenyl)$_2$ zirconium dichloride
No. 5: (Me$_2$Si)$_2$ (3-methyl-5-iso-propylcyclopentadienyl)$_2$ zirconium dichloride
No. 6: (1,2'-Me$_2$Si) (2,1'-Me$_2$Si) (3,5-diisopropylcyclopentadienyl) (indenyl) zirconium dichloride Example 6

Polymerization was carried out in the same manner as in Example 5 except for using (1,1'-Me$_2$Si)(2,2'-(i-Pr)$_2$NB)(3,5-diisopropylcyclopentadienyl)(indenyl)zirconium dichloride obtained in Example 2 as the transition metal compound.

45.5 g of polypropylene was obtained, which had an intrinsic viscosity of 1.76 dl/g, Mw of 172,000, Mw/Mn of 2.11, and a pentad meso fraction [mmmm] of 10.2%.

Example 7

Polymerization was carried out in the same manner as in Example 5 except for using (1,1'-Me$_2$Si)(2,2'-PhP)bis(indenyl)zirconim dichloride obtained in Example 3 as the transition metal compound.

The yield of the resulting polypropylene was 0.8 g and the intrinsic viscosity was 0.22 dl/g.

Example 8

Polymerization was carried out in the same manner as in Example 5 except for using (1,1'-Me$_2$SiSiMe$_2$)(2,2'-(i-Pr)$_2$NB)bis(indenyl)zirconium dichloride obtained in Example 4 as the transition metal compound.

The polypropylene obtained at a yield of 108.0 g had an intrinsic viscosity of 1.81 dl/g and a pentad meso fraction [mmmm] of 23.5%.

Example 9

Ethylene Polymerization

A 1 l autoclave, which was heated and dried, was charged with 400 ml of toluene and 5 mmol of triisobutylaluminum at room temperature in a nitrogen atmosphere.

The mixture was heated to 50° C. with stirring. Then, 10 mmol of methyl aluminoxane and 10 μmol of (1,1'-Me$_2$Si)(2,2'-PhP)(3-methyl-5-isopropylcyclopentadienyl)$_2$zirconium dichloride obtained in Example 1 were added thereto.

The mixture was polymerized for 10 minutes while controlling the pressure at 0.8 MPa with ethylene. After the polymerization reaction, the reaction product was charged into methanol. After sufficiently stirring, the resulting precipitate was collected by filtration, sufficiently washed with methanol, and dried to obtain 6.7 g of polyethylene. The intrinsic viscosity of this polyethylene was 1.02 dl/g.

Example 10

Polymerization of Higher α-Olefin

A 10 l autoclave, which was heated and dried, was charged with 3 l of 1-octadecene (C$_{18}$ α-olefin) and 3 l of heptane. The mixture was heated to the polymerization temperature of 80° C. Then, 5 mmol of triisobutylaluminum, 20 μmol of (1,1'-Me$_2$SiSiMe$_2$)(2,2'-(i-Pr)$_2$NB)bis(indenyl)zirconium dichloride obtained in Example 4, and 40 μmol of dimethylanilinium tetrakis(pentafluorophenyl)borate were added thereto. Hydrogen under a pressure of 0.8 MPa was introduced to polymerize the monomers for six hours.

After the polymerization reaction, the reaction product was charged into acetone to collect precipitate by filtration. The precipitate was dried with heating under reduced pressure to obtain 1.4 kg of a higher α-olefin polymer.

The higher α-olefin polymer was subjected to the following evaluations.

(1) Melting Point (Tm: ° C.), Heat of Fusion (ΔH: J/g)

Using a differential scanning calorimeter ("DSC-7" manufactured by Perkin-Elmer Corp.), 10 mg of the sample was retained at 190° C. for 5 minutes in a nitrogen atmosphere, cooled to −10° C. at a rate of 5° C./min, retained at −10° C. for five minutes, then heated to 190° C. at a rate of 10° C./min. A peak top melting point (Tm) observed in the heat of fusion (ΔH) curve was measured.

(2) Half Width (Wm: ° C.)

The peak width at the 50% height of the endothermic peak obtained in the melting point (Tm) measurement in DSC was measured.

(3) Weight Average Molecular Weight (Mw) and Molecular Weight Distribution (Mw/Mn)

Molecular weight was measured by the GPC method using the following instrument under the following conditions to determine the polystyrene-reduced weight average molecular weight (Mw) and number average molecular weight (Mn).

GPC measurement apparatus

Column: TOSO GMHHR1-H(S)HT

Detector: RI detector for liquid chromatogram WATERS 150C

Measurement conditions

Solvent: 1,2,4-trichlorobenzene

Measurement temperature: 145° C.

Flow rate: 1.0 ml/min.

Concentration of sample: 2.2 mg/ml

Injection amount: 160 µl

Calibration curve: Universal Calibration

Analysis program: HT-GPC (Ver. 1.0)

(4) Stereoregularity Index Value (M2: mol %)

A method proposed by T. Asakura, M. Demura, and Y. Nishiyama (Macromolecules, 24, 2334 (1991)) was followed.

Specifically, M2 was determined by utilizing the characteristics of the carbon in the α-position $CH_2$ on the side chain originating from a higher α-olefin being observed in split peaks in the $^{13}$C-NMR spectrum due to differences of stereoregularity.

$^{13}$C-NMR spectrum measuring instrument and conditions

Instrument: EX400 manufactured by JEOL Ltd.

Measurement temperature: 130° C.

Pulse width: 45°

Integration: 1000 times

Solvent: 90:10 (volume ratio) mixed solvent of 1,2,4-trichlorobenzene and benzene-$d_6$ Calculation of stereoregularity index value (M2)

Six large absorption peaks based on the mixed solvent are seen in the range from 127 to 135 ppm. Among these peaks, the value of the fourth peak from the lower magnetic field side was set to 131.1 ppm and regarded as the standard of the chemical shift.

In this instance, the absorption peak originating from the carbon in the α-position $CH_2$ on the side chain was observed in the neighborhood of 34 to 37 ppm. M2 (mol %) is determined using the following formula.

$M2$=[(integrated intensity of 36.2-35.3 ppm)/(integrated intensity of 36.2-34.5 ppm)]×100

(5) X1 (°), X1 Intensity Ratio (%)

(Method for Measuring Wide Angle X-ray Scattering Intensity Distribution)

Using an anticathode Rotor Flex RU-200 manufactured by Rigaku Corp., a monochromatic light of CuK α-ray (wavelength=1.54 Å) with an output of 30 kV and 100 mA was collimated by a 1.5 mm pinhole. Wide angle X-ray scattering (WAXS) intensity distribution was measured after one minute exposure using a position sensitive proportional counter.

The evaluation results are shown in Table 2.

TABLE 2

| Evaluation item | Measured value |
| --- | --- |
| Tm (° C.) | 39 |
| ΔH (J/g) | 114 |
| Wm (° C.) | 6.3 |
| Mw: PS-reduced | 4,000 |
| Mw/Mn: PS-reduced | 1.3 |
| M2 (mol %) | 36 |
| X1 (°) | 21 |
| X1 intensity ratio (%) | 100 |

Comparative Example 1

Polymerization of Propylene Using $(Me_2Si)_2$(3-methyl-5-iso-propylcyclopentadienyl)$_2$zirconium dichloride A 1 l autoclave, which was heated and dried, was charged with 400 ml of toluene and 0.5 mmol of triisobutylaluminum at room temperature in a nitrogen atmosphere. The mixture was heated to 50° C. with stirring. Then, 1 mmol of methyl aluminoxane and 1 µmol of $(Me_2Si)_2$(3-methyl-5-iso-propylcyclopentadienyl)$_2$zirconium dichloride were added thereto.

The mixture was polymerized for 60 minutes while controlling pressure at 0.7 MPa with propylene. After the polymerization reaction, the reaction product was charged into methanol. After sufficiently stirring, the resulting precipitate was collected by filtration, sufficiently washed with methanol, and dried to obtain polypropylene.

117 g of the product with an intrinsic viscosity of 0.94 dl/g was obtained.

Comparative Example 2

Polymerization of Propylene Using (1,2'-$Me_2Si$)(2,1'-$Me_2Si$)(3,5-diisopropylcyclopentadienyl)(indenyl)zirconium dichloride A 1 l autoclave, which was heated and dried, was charged with 400 ml of toluene and 0.5 mmol of triisobutylaluminum at room temperature in a nitrogen atmosphere. The mixture was heated to 50° C. with stirring. Then, 1 mmol of methyl aluminoxane and 1 µmol of $(Me_2Si)_2$(3,5-diisopropylcyclopentadienyl)(1,2'-indenyl)zirconium dichloride were added thereto.

The mixture was polymerized for 30 minutes while controlling pressure at 0.7 MPa with propylene. After the polymerization reaction, the reaction product was charged into methanol. After sufficiently stirring, the resulting precipitate was collected by filtration, sufficiently washed with methanol, and dried to obtain polypropylene.

9.93 g of the product with an intrinsic viscosity of 0.24 dl/g was obtained.

INDUSTRIAL APPLICABILITY

The transition metal compound of the invention is useful as a catalyst for olefin polymerization. A high molecular weight polyolefin possessing regularity can be obtained by using a catalyst for olefin polymerization containing the transition metal compound.

The invention claimed is:
1. A transition metal compound represented by formula (1),

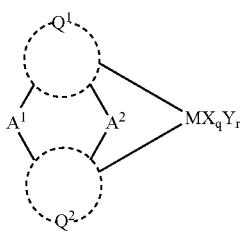
(1)

wherein M is a metal element of the groups 3 to 10 of the Periodic Table or a lanthanoid;
  X represents a ligand having a sigma bond for binding to M, and when X is plural, the Xs may be the same or different;
  Y represents a Lewis base, and when Y is plural, the Ys may be the same or different;
  $A^1$ and $A^2$ represent crosslinking groups and at least one thereof has a boron or phosphorous atom as a crosslinking atom, the crosslinking group having a boron atom as a crosslinking atom is represented by the formula (4) and the crosslinking group having a phosphorous atom as a crosslinking atom is represented by formula (5);
  q is an integer of 1 to 5 and equals [(the valance of M)–2];
  r is an integer of 0 to 3; and
  $Q^1$ and $Q^2$ have a structure represented by formula (2) or (3), and $Q^1$ and $Q^2$ may be different or the same,

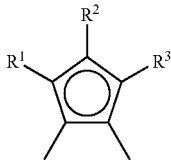
(2)

wherein $R^1$ to $R^3$ are a hydrogen atom, a halogen atom, a hydrocarbon group with 1 to 20 carbon atoms, a halogen-containing hydrocarbon group with 1 to 4 carbon atoms, a silicon-containing group or a hetero-atom-containing group,

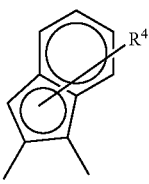
(3)

wherein $R^4$ is a hydrogen atom or a hydrocarbon group with 1 to 20 carbon atoms,

(4)

wherein E is a boron atom; and
  $R^5$ is an electrically neutral basic group containing nitrogen, oxygen, phosphorous or sulfur, or a group having a negative charge containing $N^-$,

(5)

wherein E is a phosphorous atom;
  $R^5$ is a hydrocarbon group having 1 to 20 carbon atoms; and
  $R^6$ is =N—$R^7$ (wherein $R^7$ is an alkyl group, alkenyl group, arylalkyl group or aryl group) or =S.

* * * * *